United States Patent [19]

Kuroda et al.

[11] 4,416,777
[45] Nov. 22, 1983

[54] SEPARATION OF LEUKOCYTES OR LYMPHOCYTES FROM LEUKOCYTE-CONTAINING SUSPENSION

[75] Inventors: Toru Kuroda, Fuji; Yoshinori Takenaka, Saitama; Nobuaki Tsuda, Fuji, all of Japan

[73] Assignee: Asahi Kasei Kogyo Kabushiki Kaisha, Osaka, Japan

[21] Appl. No.: 193,571

[22] Filed: Oct. 3, 1980

[30] Foreign Application Priority Data

Oct. 9, 1979 [JP] Japan ............................... 54-129482

[51] Int. Cl.³ ...................... B01D 39/02; B01D 37/02
[52] U.S. Cl. .................................... 210/446; 55/524; 55/527; 210/509; 210/927; 210/504; 436/177
[58] Field of Search ............... 210/927, 509, 508, 193, 210/446, 639, 504; 428/289, 290; 55/524, 527, 528; 436/177

[56] References Cited

U.S. PATENT DOCUMENTS 2,195,272  3/1940  Ehlers ................................. 210/509
2,834,730  5/1958  Painter, Jr. ......................... 210/504
4,256,588  3/1981  Hoehn et al. .................. 210/927 X
4,301,118  11/1981  Eddleman et al. ................. 210/927

FOREIGN PATENT DOCUMENTS 54-98095   8/1979  Japan ................................. 210/509
54-122713  9/1979  Japan ................................. 210/927

Primary Examiner—Michael S. Marcus
Attorney, Agent, or Firm—Sprung, Horn, Kramer & Woods

[57] ABSTRACT

Leukocytes are separated from a leukocyte-containing suspension by bringing the leukocyte-containing suspension into contact with a leukocyte-separating material, whereby a substantial part of the leukocytes are entrapped in the leukocyte-separating material, and then, collecting the entrapped leukocytes. The leukocyte-separating material used comprises a fibrous material having a surface layer composed of a substance which is capable of being dissolved in water by degrees. Lymphocytes can also be separated in a manner similar to that mentioned above, from a lymphocyte-containing suspension having reduced contents of granulocytes and monocytes.

19 Claims, 12 Drawing Figures

SEPARATION OF LEUKOCYTES OR LYMPHOCYTES FROM LEUKOCYTE-CONTAINING SUSPENSION

BACKGROUND OF THE INVENTION (1) Field of the Invention

This invention relates to separation of leukocytes or lymphocytes from a leukocyte-containing suspension. More particularly, it relates to a material used for separating leukocytes or lymphocytes from a leukocyte-containing suspension, a method of such separation and a filter comprising the material used for such separation.

By the term "leukocyte-containing suspension" used herein is meant blood and other leukocyte-containing body fluids. This term should also be interpreted as including physically, chemically and/or biologically treated blood and other body fluids such as, for example, blood diluted with a physiological solution and erythrocyte agglutinant-(such as dextran or hydroxyethyl-starch)-incorporated blood.

(2) Description of the Prior Art

Due to recent developments in haematology and immunology, blood component transfusions, tests of leukocytes, inspections of surface antigens of leukocytes and measurements of subpopulation ratios of lyphocytes have frequently been performed and results of these inspections have been used to remedy and diagnose various diseases. Moreover, tests to classify and separate sub-sets such as helper T-cells and suppressor T-cells have been made at various hospitals and research institutes As the conventional method of entrapping and collecting leukocytes or lymphocytes applicable to the foregoing uses, there can be mentioned a method using an erythrocyte-agglutinant, a centrifugal separation method and a method utilizing adhesion of leukocytes or lymphocytes to fibers.

According to the method using an erythrocyte-agglutinant, dextran, hydroxyethyl starch or other erythrocyte-agglutinant is added to blood, the blood is allowed to stand for a certain time and, then, a supernatant rich in leukocytes is recovered. According to the centrifugal separation method, blood is subjected to centrifugal separation and a buffy coat rich in leucocytes is collected, and according to the density gradient centrifugal separation method, blood is superposed on a liquid having a specific gravity of 1.077, the superposed layers are centrifuged and the lymphocyte-containing layer is recovered. As the known method utilizing adhesion of leukocytes or lymphocytes to fibers, there can be mentioned a method causing monocytes and granulocytes to adhere to fibers and recovering the adhering hematocytes by using a physiological saline solution or a phosphoric acid-buffered physiological saline solution, and a method comprising preparing a fraction rich in leukocytes by using a coagulant or a centrifugal separator, introducing the leukocyte-rich fraction into a column packed with fibers of nylon or glass wool, maintaining the fraction at 37° C. for about 30 minutes in the column and finally recovering lymphocytes therefrom.

However, these known methods are not satisfactory in that relatively large quantities of erythrocytes and platelets are contained in the collected leukocyte or lymphocyte fractions. If large quantities of erythrocytes and platelets are contained, large errors are frequently caused during various inspections using leukocytes and lymphocytes, and inspections often become impossible.

More specifically, in the method using an erythrocyte-agglutinant, the number of incorporated erythrocytes is from several to about 15 times as large as the number of leukocytes, and the number of incorporated platelets is scores of times as large as the number of leukocytes. In the centrifugal separation method using a buffy coat, the number of incorporated erythrocytes and platelets is several to about 15 times the number of leukocytes, and in the density gradient centrifugal separation method, the number of incorporated platelets is from several times as large as the number of lymphocytes. In the density gradient centrifugal separation method, the number of erythrocytes can be reduced to less than 1/10 of the number of lymphocytes. However, in the case where the specific gravity is reduced in some of the erythrocytes, as in blood of patients, the number of erythrocytes is often several to about 15 times the number of lymphocytes. Furthermore, since the operation is complicated and a substantially long time is required for completion of separation, the obtained leukocytes are damaged and reduction of the functions of the leukocytes or reduction of the survival ratio of the leukocytes is often observed. In the method utilizing adhesion of hematocytes to fibers, the number of ertythrocytes or platelets is often several to about 15 times the number of lymphocytes or granulocytes.

SUMMARY OF THE INVENTION

It is therefore the main object of the present invention to enable the separation of leukocytes or lymphocytes from a leukocyte-containing suspension while the incorporation of other components such as erythrocytes and platelets into the collected leukocyte- or lymphocyte-rich suspension is minimized.

Other objects and advantages of the present invention will become apparent from the following description.

In accordance with a first aspect of the present invention, there is provided a material for separating luekocytes from a leukocyte-containing suspension comprising a fibrous material having a surface layer composed of a substance which is capable of being dissolved in water by degrees.

In accordance with a second aspect of the present invention, there is provided a process for separating leukocytes from a leukocyte-containing suspension, which comprises bringing the leukocyte-containing suspension into contact with the leukocyte-separating material, specified above, whereby a substantial part of leukocytes are entrapped in the leukocyte-separating material, and then, collecting the leukocytes entrapped in the leukocyte-separating material.

In accordance with a third aspect of the present invention, there is provided a filter for separating leukocytes from a leukocyte-containing suspension, which comprises the leukocyte-separating material, specified above, packed in a container.

In accordance with a fourth aspect of the present invention, there is provided a process for preparing a filter for separating leukocytes from a leukocyte-containing suspension, which comprises the steps of:

packing a container with open fibers, bringing the packed fibers into contact with a coating solution, removing the surplus amount of the coated solution from the packed fibers, and then drying the coated solution.

In accordance with a fifth aspect of the present invention, there is provided a process for separating lymphocytes from a lymphocyte-containing suspension having reduced contents of granulocytes and monocytes, which comprises bringing the lymphocyte-containing suspension into contact with the leukocyte-separating material, specified above, whereby a substantial part of lymphocytes are entrapped in the leukocyte-separating material, and then, collecting the lymphocytes entrapped in the leukocyte-separating material.

In accordance with a sixth aspect of the present invention, there is provided a lymphocyte-separating filter, which comprises at least one container packed with fibers and having at least two inlet and outlet openings, said container or containers having a first portion composed of fibers having an average diameter of from 5 to 20 microns, which fibers are packed at a bulk density of from 0.04 to 0.4 g/cm³ and which fibers have a surface layer composed of a substance capable of being dissolved in water by degrees, and a second portion arranged in series to said first portion and composed of fibers having an average diameter larger than the average diameter of the fibers of the first portion and in the range of from 10 to 60 microns.

BRIEF DESCRIPTION OF THE DRAWINGS

This invention will now be described with reference to the accompanying drawings, in which.

DESCRIPTION OF THE PREFERRED EMBODIMENTS

The leukocyte-separating material of this invention will first be described.

By the term "fibrous material" is meant a material composed of fibers having a length much larger than the average diameter thereof, and the average diameter (D) is defined by the following equation:

$$D \text{ (cm)} = 2\sqrt{\frac{x}{\pi \rho y}}$$

where x stands for the weight (g) of the fibers, y stands for the length (cm) of the fibers and $\rho$ stands for the density (g/cm³).

The average diameter of the fibrous material is not particularly critical, but when monocytes and granulocytes are especially separated among leukocytes, it is preferred that the average diameter be not larger than 60 microns and in order to entrap leukocytes at an enhanced efficiency, it is especially preferred that the average diameter be not larger than 10 microns. From the viewpoint of the efficiency of recovery of entrapped leukocytes, it is preferable that the average diameter be in the range of from 5 to 10 microns.

The fibrous material used is not partcularly critical, so far as it does no harm to leukocytes and a coating substance layer capable of being gradually dissolved in water can be formed thereon. For example, synthetic fibers such as polyacrylonitrile fibers, polyether fibers and polyamide fibers; semi-synthetic fibers such as cellulose acetate fibers; regenerated cellulose fibers such as cuprammonium rayon fibers; natural fibers such as cotton; and inorganic fibers such as glass fibers can be used.

In the present invention, it is indispensable that a surface layer formed on the fibrous material should be capable of being dissolved in water by degrees. If this property is expressed in terms of the dissolution rate, it is preferred that the dissolution rate of the surface layer in water be in the range of from 0.3 to 1.0 mg/min·cm², particularly from 0.4 to 0.9 mg/min·cm².

By the term "dissolution rate" used herein is meant a value determined according to the following measurement method.

Figure 1:
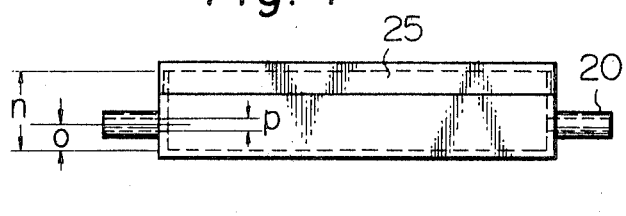
FIG. 1 is a front view illustrating a vessel that is used for measuring the dissolution rate of a coating substance.
Figure 2:
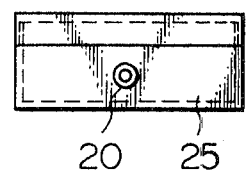
FIG. 2 is a side view of the vessel illustrated in FIG. 1.
Figure 3:
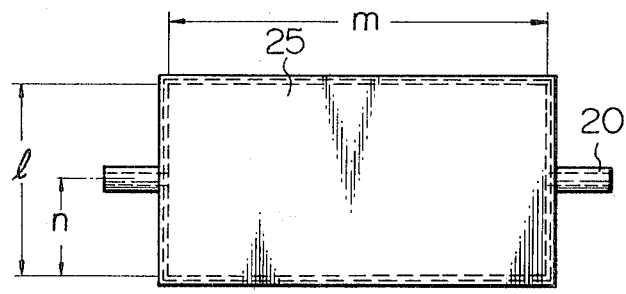
FIG. 3 is a top plan view of the vessel illustrated in FIG. 1.

A vessel 25 as illustrated in FIGS. 1 through 3 is used for the measurement. FIG. 1 is a front view of the vessel, FIG. 2 is a side view of the vessel, and FIG. 3 is a top plan view of the vessel. This vessel has an inner length (l) of 30 mm, an inner width (m) of 61 mm and an inner depth (n) of 15 mm, and water flow pipes 20 having an inner diameter (p) of 2 mm are placed in the centers of both side faces at a position 5 mm high from the inner bottom of the vessel.

A coating layer of a substance to be measured, having a surface area of 18.3 cm² and a uniform thickness, is formed on the inner bottom face of the vessel. The substance to be tested is used in such an amount that the total weight of the coating layer that can be dissolved out is 200 mg.

The method of forming this coating layer is not particularly critical. For example, there can be adopted a method in which a water-soluble substance is coated on the inner bottom face of the vessel (in principle, the vessel is composed of the same material as that of the fibrous material) and a method in which a water-soluble substance is physically and/or chemically held on the inner bottom face of the vessel composed of the same material as that of the fibrous material.

An instance of the method of coating the inner bottom face of the vessel with a water-soluble substance will now be described.

First, 2 ml of an aqueous solution containing the substance to be tested at a concentration of 10 g/dl was placed in the vessel and spread entirely over the inner bottom face of the vessel. Then, the vessel in sufficiently dried at 37° C. in an incubator in the state where a lid is not attached to the vessel, whereby the intended coating layer is formed. When a substance providing a readily cracking coating layer is used, mild conditions, for example, drying at room temperature, are adopted and attention should be paid so that a homogeneous coating is formed.

Figure 4:
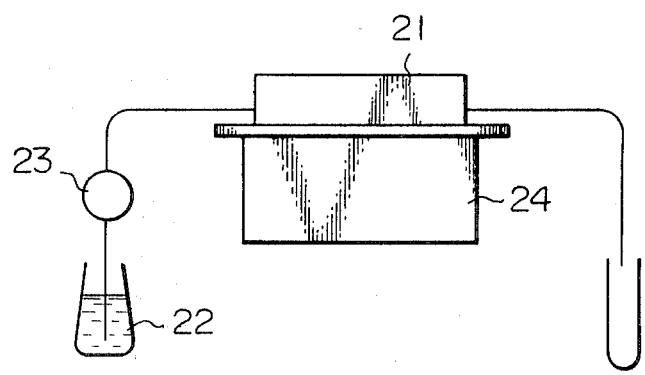
FIG. 4 is a diagram illustrating an experimental apparatus that is used for measuring the dissolution rate of a coating substance.

Then, the vessel having the coating layer formed on the bottom face is set at a measurement apparatus illustrated in FIG. 4. In FIG. 4, reference numerals 21, 22, 23 and 24 represent a vessel having a coating layer formed on the bottom face, a water-filled beaker, a pump and a shaking machine, respectively. Water maintained at 30° C. is fed at a flow rate of 5 ml/min into the vessel 21 from the beaker 22, and aqueous solution containing the substance to be tested, which comes out of the vessel 21, is sampled and the amount of the test substance dissolved out for a predetermined time is measured. At this measurement, the vessel 21 is kept in the horizontal posture and water in the vessel 21 is always shaken by the shaking machine 24. Shaking is performed by a horizontal 8-figured movement such that one reciprocative movement of 3 cm per second is given in the water-flowing direction of y ($y = 1.5 \cos 2\pi t$(cm), in which t stands for the time in second) and two reciprocative movements of 2 cm are given in the direction of x, rectangular to the water-flowing direction of y ($x = -\sin 4\pi t$(cm), in which t stands for the time in second). The test substance-containing solution coming out of the vessel is sampled at intervals of, for example, 4 minutes (at every 20 ml of the volume rate in flow) and the dissolution pattern with respect to the time is drawn.

Figure 5:
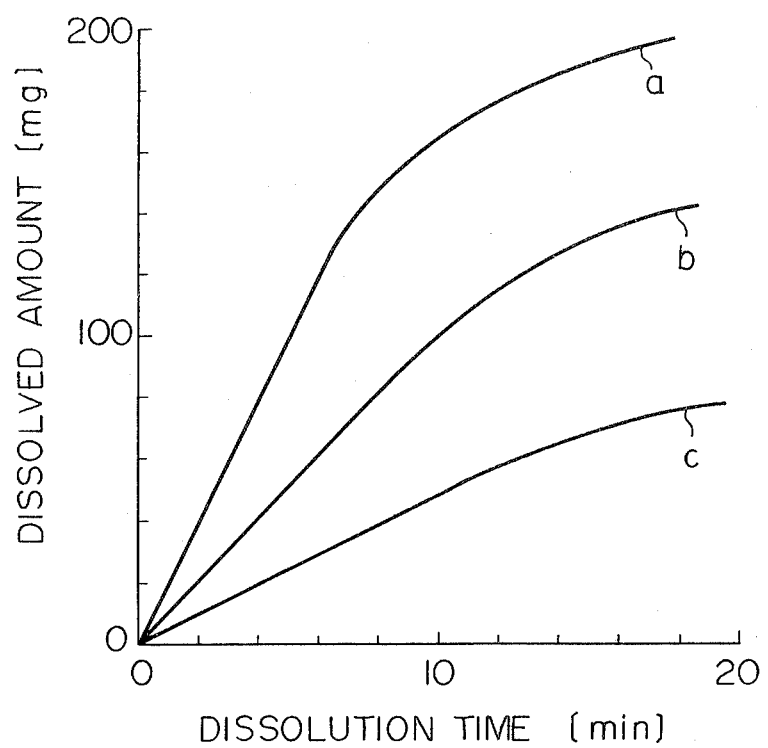
FIG. 5 is a graph illustrating the dissolution rates of typical coating substances.

The so-drawn dissolution patterns of the test substances are as exemplified in FIG. 5. In FIG. 5, curve "a" shows the dissolution pattern of a substance having a high dissolution rate, and the dissolution rates of substances illustrated by curves "b" and "c" are lower than that of curve a. In the present invention, the dissolution rate is defined as a value calculated from the amount of the test substance having a certain surface area (18.3 cm$^2$), which is dissolved out at the point of a dissolution time of 8 minutes, in the vicinity of which a good linearity is maintained in each dissolution pattern curve. That is, in the present invention, the dissolution rate is defined by the following equation:

Dissolution rate (kg/min·cm$^2$) = [amount dissolved (mg) of substance at dissolution time of 8 minutes] ÷ [8 minutes × 18.3 cm$^2$](mg/min·cm$^2$) (in which the amount of the test substance dissolved is measured according to the above-mentioned method)

The effect of inhibiting adhesion of erythrocytes or platelets to the leukocyte-separating material can be obtained by the surface layer (hereinafter referred to as "erythrocyte adhesion-inhibiting surface layer") capable of being dissolved in water at the above-mentioned specific dissolution rate determined according to the above-mentioned method. It is believed that the reason is that, since the surface layer gradually flows out from the surface of the fibrous material, erythrocytes having a high deformability and platelets which are small in size and light are not liable to adhere to the fibrous material but leukocytes having a low deformability, a relatively heavy weight and a relatively large spherical shape are allowed to adhere to the fibrous material with relative ease.

If the dissolution rate of the coating layer is too low, the amount of the coating layer flowing out from the fibrous material is too small and the above-mentioned effect is very low. In contrast, if the dissolution rate of the coating layer is too high, the coating layer flows out from the fibrous material too quickly and the coating layer is lost from the fibrous material in a very short time.

Under ordinary operation conditions, therefore, it is preferred that the dissolution rate of the erythrocyte adhesion-inhibiting surface layer be in the range of from 0.3 to 1.0 mg/min·cm$^2$, more preferably from 0.4 to 0.9 mg/min·cm$^2$, as mentioned hereinbefore. Of course, even if the dissolution rate of the surface layer is outside this preferred range, adhesion of erythrocytes and platelets to the leukocyte-separating material can be inhibited by appropriately controlling the operation conditions such as the blood quantity, the washing quantity and the flow rate.

More specifically, in case of a surface layer having a dissolution rate of higher than 1.0 mg/min·cm$^2$ in water, that is, a surface layer which is dissolved in water in a shorter time, adhesion of erythrocytes or platelets to the leukocyte-separating material can be prevented by increasing the thickness of the surface layer formed on the surface of the fibrous material, reducing the amount of blood to be treated, increasing the flow rate or lowering the temperature. The reason is that if the surface layer formed on the surface of the fibrous material is being dissolved into blood only while erythrocytes or platelets are allowed to fall in contact with the leukocyte-separating material, the erythrocytes and platelets are not liable to be allowed to adhere to the surface of the fibrous material. However, in the actual operation, the thickness of the surface layer formed on the surface of the fibrous material is limited, and if the flow rate of blood is increased, leukocytes tend to easily leak from the leukocyte-separating material and the recovery ratio of leukocytes is lowered. Therefore, it is preferred that the dissolution rate of the erythrocyte adhesion-inhibiting surface layer be not higher than 1.0 mg/min·cm$^2$.

In case of a surface layer having a dissolution rate of lower than 0.3 mg/min·cm$^2$, that is, a surface layer which is not readily dissolved out into water even for a long time, if the dissolution of the surface layer into blood is enhanced by applying physical vibrations or elevating the temperature, erythrocytes or platelets are not liable to be allowed to adhere to the leukocyte-separating material. However, in the practical operation, if physical vibrations are applied, leukocytes tend to leak from the leukocyte-separating material and the recovery ratio of leukocytes is reduced, and if the temperature is elevated excessively, blood is readily modified. It is therefore preferred that the dissolution rate of the surface layer be at least 0.3 mg/min·cm$^2$.

The material of the erythrocyte adhesion-inhibiting coating layer formed on the fibrous material is not particularly critical, so far as it does no harm to leukocytes. For example, there can be mentioned gelatin, casein, polyvinylpyrrolidone, polyvinylalcohol and polyvinyl methyl ether.

The method of forming an erythrocyte adhesion-inhibiting surface layer is not particularly critical. For example, there can be adopted a method in which a substance soluble in water is coated on the surface of the fibrous material and a method in which a substance soluble in water is physically or chemically held on the surface of the fibrous material. The former method comprising coating a substance soluble in water on the surface of the fibrous material will now be described by way of example. A coating can be formed by bringing an isotonic solution of a substance constituting the erythrocyte adhesion-inhibiting surface layer into contact with the surface of the fibrous substrate. It is sufficient if the amount of the erythrocyte adhesion-inhibiting surface layer applied to the surface of the substrate is at least such that a monomolecular layer will be formed. It is not always indispensible that the surface layer should be adsorbed in the fibrous material. In short, the amount of the coating applied to the surface of the fibrous material is appropriately decided according to the amount of blood, the amount of the washing solution, the flow rate and other conditions under which the resulting separating material is actually used. Furthermore, a separating material formed by applying a substance constituting the erythrocyte adhesion-inhibiting surface layer to the surface and drying the coated surface in advance may be used, and this separating material is excellent in maintaining the sterile condition and ease in handling when the separating material is actually used. However, it is often preferred that the surface layer present on the surface of the fibrous material be kept in the wet state when blood or the like is brought into contact with the leukocyte-separating material.

As will be apparent from the foregoing illustration, the leukocyte-separating material according to this invention comprising a fibrous substrate and an erythrocyte adhesion-inhibiting surface layer formed on the surface of the fibrous material.

A leukocyte-separating filter according to the present invention, which will now be described, comprises a container and the above-mentioned leukocyte-separating material packed in the container. In this filter, it is preferred that the leukocyte-separating material be sufficiently opened and disentangled. More specifically, it is preferred that the bulk density of the leukocyte-separating material be in the range of from 0.04 g/cm$^3$ to 0.4 g/cm$^3$ in the dry state. If the bulk density is too low, leukocytes cannot sufficiently be entrapped and the leukocyte recovery ratio is reduced. On the other hand, if the bulk density is too high, leukocytes are entrapped sufficiently but such disadvantages as reduction of the recovery ratio and increase of erythrocytes left in the filter are brought about. It is especially preferred that the bulk density be in the range of from 0.04 g/cm$^3$ to 0.25 g/cm$^3$.

Figure 6:
FIG. 6 is a schematic sectional view illustrating a leukocyte-separating filter constructed by packing a leukocyte-separating material of the present invention in a container.

The leukocyte-separating filter including the leukocyte-separating material according to the present invention is constructed, for example, as illustrated in FIG. 6. Referring to FIG. 6, a leukocyte-separating material 1 such as mentioned above is packed in a water-resistant container 2 having liquid inlet and outlet openings 2 and 3. Mesh sieves 5 and 6 are disposed to prevent the leukocyte-separating material from leaking out from the container 4.

The process for preparing such leukocyte-separating filter including the leukocyte-separating material according to the present invention will now be described.

The leukocyte-separating filter may be constructed by forming a leukocyte-separating material comprising a fibrous material and a surface layer capable of being gradually dissolved in water, which is formed on the surface of the fibrous material, and packing the leukocyte-separating material in a container. However, when the leukocyte-separating material is formed by coating a fibrous material with a substance capable of being gradually dissolved in water, it is recommended to adopt the following process for the preparation of the leukocyte-separating filter.

That is, a fibrous material is opened and then packed in a container, a solution of a coating-forming substance is brought into contact with the fibrous material, the surplus amount of the coating substance solution over the necessary amount thereof is removed from the surface of the fibrous material, and the coated fibrous material is then dried, whereby the intended leukocyte-separating filter is obtained.

According to this filter-preparing process, a homogeneous surface layer is formed on the surface of the fibrous material which has been sufficiently opened, and even intersecting points of fibers can be coated satisfactorily. Moreover, since any mechanical external force need not be applied after drying of the surface layer, undesirable peeling or cracking of the surface layer is not caused.

The preparation conditions will now be described more in detail.

Formation of a surface layer on the surface of the fibrous material in the container may be accomplished only by filling a coating substance solution into the container or by circulating the coating substance solution in the container. In short, it is sufficient if the coating substance solution is brought into contact with the surface of the fibrous material and with the inner face of the container. With some coating substances, reaction of the coating substance with the fibrous material may be advanced at this step.

After the coating substance solution has been brought into contact with the surface of the fibrous material, the surplus amount of the coating substance over the necessary amount is removed from the surface of the fibrous material. This removal is accomplished by a centrifuging method comprising applying a centrifugal force of a centrifugal separator entirely to the container and moving away the surplus coating substance by this centrifugal force, a method comprising blowing away the surplus amount of the coating substance by compressed air, a method comprising washing away the surplus amount of the coating substance with a solvent, and a method comprising freeze-drying the coating layer to separate the coating substance present in the surface of the fibrous material from the coating substance present apart from the surface of the fibrous material. From the viewpoints of the uniformity of the surface layer formed on the surface of the fibrous material, ease in adjustment of the thickness of the surface layer and the time necessary for completion of the drying step, the centrifuging method is most preferable and recommended.

In this centrifuging method, it is preferred that the centrifugal force applied be in the range of from $50 \times g$ to $500 \times g$. If the centrifugal force is smaller than $50 \times g$, the coating substance is often left non-uniformly in the filter. If the centrifugral force exceeds $500 \times g$, the fibrous material tends to shrink. However, shrinkage of fibers can be removed simply be application of an external force. Accordingly, a centrifugal force exceeding 500×g may be applied.

This method can be adopted only after the fibrous material has been packed in the container. If this method is adopted before the fibrous material is packed in the container, fibers of the opened fibrous material adhere to one another or they are crushed, and therefore, opening should be conducted again. Furthermore, a good open state cannot be obtained even by conducting opening again. In contrast, if the above method is adopted after packing of the open fibrous material in the container, even when the pack density of the fibrous material is low, the fibrous material is not liable to be caused to shrink by virtue of the frictional resistance between the wall of the container and the fibrous material or the restoring force of entangled fibers of the fibrous material, and even if shrinkage of the fibrous material is caused, the original state can easily be restored by using compressed air or the like. The thickness of the surface layer is adjusted by the concentration of the coating substance solution or the intensity of the centrifugal force and is appropriately determined according to the physical properties and chemical properties of the coating substance and the properties of the solvent used. Any drying method capable of removing the solvent, such as vacuum drying or hot air drying, can be adopted. The drying conditions are such that the coating substance is not modified or dissolved.

An embodiment of the leukocyte-separating process according to the present invention will now be described.

Figure 7:
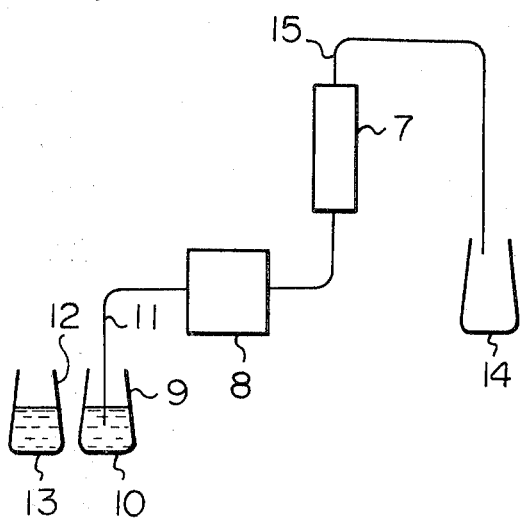
FIG. 7 is a diagram illustrating an embodiment of the apparatus for use in carrying out the leukocyte-separating process according to the present invention.

Referring to FIG. 7, a leukocyte-separating filter 7 is constructed by packing the leukocyte-separating material according to the present invention in a container. In this embodiment, the leukocyte-separating material in the leukocyte-separating filter 7 is prepared by forming an erythrocyte adhesion-inhibiting coating layer on the surface of a fibrous material and is kept in the dry state. At first, a physiological solution 10 in the vessel 9 is fed to the leukocyte-separating filter 7 by means of a pump 8 to wet the surface of the leukocyte-separating material in the leukocyte-separating filter 7. Then, an inlet conduit 11 is separated from a vessel 9 of the physiological solution 10 and is connected to a vessel 12, and blood 13 in the vessel 12 is fed to the leukocyte-separating filter 7. In this leukocyte-separating filter 7, leukocytes are selectively entrapped, but plasma, erythrocytes and platelets are not liable to be entrapped and they are allowed to pass through the leukocyte-separating filter 7 and are fed to a vessel 14. The inlet conduit 11 is connected to the vessel 9 again, and the physiological solution 10 is caused to flow through the leukocyte-separating filter 7, whereby plasma, erythrocytes and platelets are substantially washed away. Accordingly, plasma and erythrocytes are not substantially left in the leukocyte-separating filter 7 and the platelets are left in very small quantities. In other words, only leukocytes are entrapped in the filter 7 substantially and selectively. In FIG. 7, reference numeral 15 represents an outlet opening of the leukocyte-separating filter.

Figure 8:
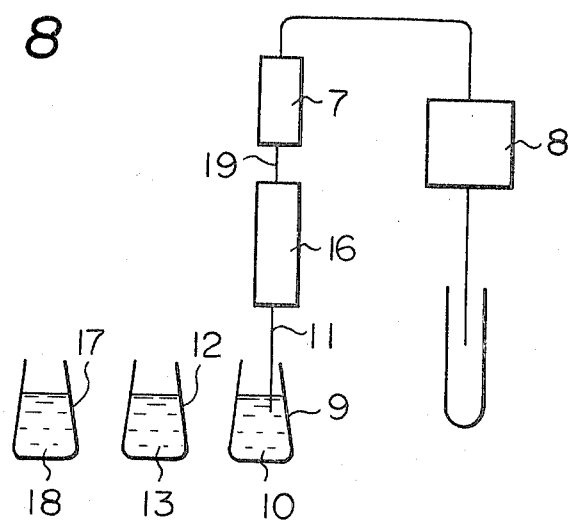
FIG. 8 is a diagram illustrating another embodiment of the apparatus for use in carrying out the leukocyte-separating process according to the present invention.

FIG. 8 illustrates an embodiment of the apparatus for collecting lymphocytes alone for determining the surface antigen of leukocytes or the sub-fraction lymphocytes. Monocytes and granulocytes in leukocytes of blood are entrapped in advance by a filter 16 for separating monocytes and granulocytes, and lymphocytes are substantially selectively entrapped in a leukocyte-separating filter 7. In FIG. 8, reference numerals 17, 18 and 19 represent a vessel, a silicone oil and an inlet conduit of the leukocyte-separating filter 7, respectively.

The technique of entrapping leukocytes alone on the filter selectively by such simple means has not been known in the art, and this is made possible for the first time by using the leukocyte-separating material according to the present invention.

Then, the leukocytes entrapped in the leukocyte-separating filter 7 are recovered while imparting physical shocks or the like to the filter, whereby the leukocytes can be recovered at a high recovery ratio and the ratios of the erythrocytes and platelets incorporated into the recovered leukocytes can be remarkably reduced.

In the case where leukocytes are separated by using a fiber-packed filter, many eryhtrocytes can be washed away by washing the filter in a physiological solution after passage of blood through it. However, since the number of erythrocytes contained in blood is about 1000 times as large as the number of leukocytes contained in blood, even if the number of erythrocytes left in the filter is reduced, the number is from several to scores of times as large as the number of leukocytes entrapped in the filter. According to the leukocyte-separating process of this invention, since the leukocyte-separating material comprising an erythrocyte adhesion-inhibiting coating layer formed on the fibrous material is used, the number of erythrocytes left in the leukocyte-separating filter can be reduced to a value of from about 1/15 to about 1/5 of the number of the entrapped leukocytes. The reason is that since the erythrocyte adhesion-inhibiting coating layer has a good dissolution rate, the erythrocyte adhesion-inhibiting surface layer is always dissolved little by little from the surface of the fibrous material and erythrocytes having a high deformability are not liable to be allowed to adhere to the surface of the fibrous material. On the other hand, it is believed that leukocytes which have a low deformability and a high adhesiveness are readily caught and entrapped at intersecting points of fibers or narrow gaps formed among fibers.

The relation between the rate of dissolution of the erythrocyte adhesion-inhibiting surface layer and the number of incorporated erythrocytes in the separation of leukocytes will now be described.

Figure 9:
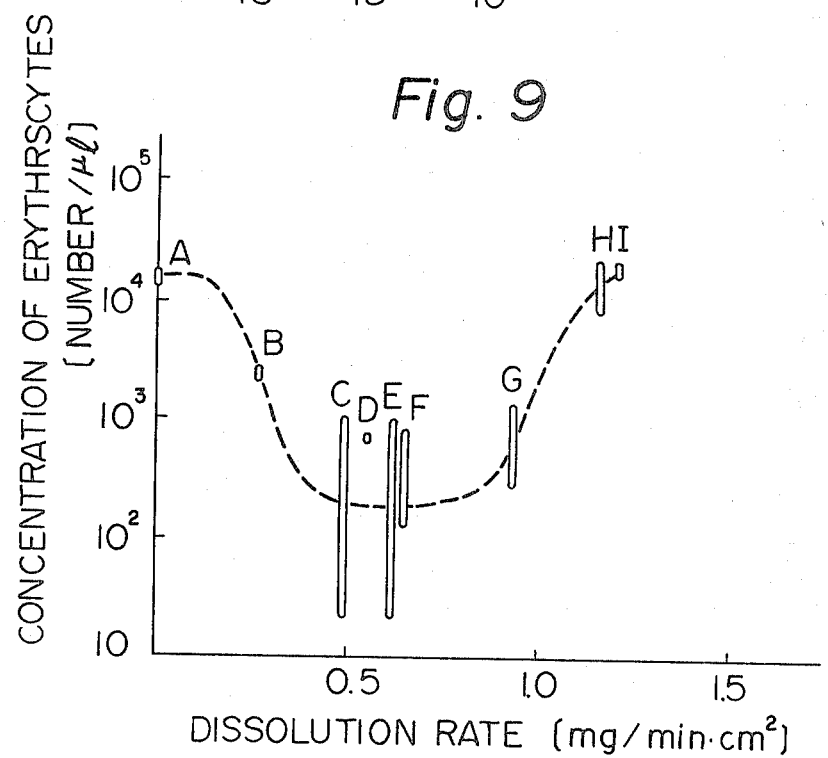
FIG. 9 is a graph illustrating the relation between the dissolution rate of a coating substance and the incorporated erythrocyte concentration observed when the leukocyte-separating operation is carried out by using fibers coated with the coating substance.

FIG. 9 is a graph illustrating the relation between the rate of dissolution of the surface layer in water and the concentration of incorporated erythrocytes. The experiment for determining this relationship was carried out according to the following procedures.

Gelatin, casein, polyvinylalcohol, polyvinylpyrrolidone, polymethyl vinyl ether and saccharide were used as a surface layer-forming substance. Substances differing in the molecular weight or those cross-linked after coating on the fibrous material were also used. Polyacrylonitrile fibers having an average diameter of 8.2 microns were used for the fibrous material. The fibers were sufficiently opened and 0.26 g of the open fibers were packed in a container having a diameter 10 mm and a length of 25 mm to form a filter. Each substance was coated on the fibrous material by forming an isotonic solution containing 3.5% of the coating substance (the concentration was reduced to 2.5% when the coating substance gave a highly viscous solution at a concentration of 3.5%) and circulating the solution through the filter at a flow rate of 5 ml/min for 5 minutes.

Separation of leukocytes was carried out according to the following procedures.

At first, 5 ml of blood was passed through the filter at a flow rate of 1 ml/min at 37° C. and then, 20 ml of physiological saline solution was passed through the filter at a flow rate of 5 ml/min. Then, 2 ml of physiological saline solution was passed through the filter at a very high speed promptly to recover entrapped leukocytes. The erythrocyte concentration in the recovered liquid was determined and was plotted on the ordinate as the incorporated erythrocyte concentration, while the dissolution rate of the coating substances determined according to the above-mentioned method was plotted on the abscissa, whereby a graph on FIG. 9 was obtained.

In FIG. 9, A shows results obtained when gelatin (insolubilized in water) was used as the surface layer-forming substance, and B, C, D, E, F, G, H and I show results obtained when polyvinylalcohol (having a degree of polymerization of 1,200), gelatin (having a molecular weight of 110,000), polymethyl vinyl ether, gelatin (having a molecular weight of 60,000) or polyvinylpyrrolidone (having a molecular weight of 36,000) or casein, polyvinylalcohol (having a degree of polymerization of 500), gelatin (having a molecular weight of 30,000), saccharide or gelatin (having a molecular weight of 4,000 to 7,000), and polyvinylpyrrolidone (having a molecular weight of 40,000) were used as the surface layer-forming substance, respectively.

From the results shown in FIG. 9, it will readily be understood that if the rate of dissolution of the coating substance in water is in the range of from 0.3 g/min·cm$^2$ to 1.0 mg/min·cm$^2$, the incorporated erythrocyte concentration is reduced below 1000/micro-liter. In order to maintain the incorporated erythrocyte concentration stably below 1000/micro-liter, it is preferred that the dissolution rate be in the range of from 0.4 mg/min·cm$^2$ to 0.9 mg/min·cm$^2$. Furthermore, it will readily be understood that even if the same coating substance, for example, polyvinylpyrrolidone or gelatin, is used, when the dissolution rate is greatly increased or decreased by changing the molecular weight or cross-linking the coating sustance, the effect of reducing the incorporated erythrocyte concentration is reduced.

This invention will now be described in detail with reference to the following Examples that by no means limit the scope of the invention.

Heparin-added blood formed by adding 5 units of heparin to 1 ml of blood collected from a healthy man was used as blood in each of the following Examples. In this blood, the number of erythrocytes was 4,100,000 to 4,800,000 per micro-liter of blood and the number of leukocytes was 5,000 to 8,500 per micro-liter of blood (The number of lymphocytes was 25 to 45% of the total number of leukocytes). The number of platelets was 130,000 to 320,000 per micro-liter of blood.

EXAMPLE 1

The experiment of separation of leukocytes was carried out by using the experimental apparatus shown in FIG. 7. At first, 0.26 g of polyacrylonitrile fibers having an average diameter of 8.2 microns were packed in a container having a diameter of 10 mm and a length of 25 mm, and an aqueous physiological saline solution containing 2.5 g/dl of polyvinylpyrrolidone (having a molecular weight of 360,000) having a dissolution rate of 0.62 mg/min·cm$^2$ in water was filled in the container to form a leukocyte-separating filter 7. Then 3 ml of heparin-added human blood was passed through the filter 7 at a flow rate of 1 ml/min by means of a pump 8 and then, 20 ml of physiological saline solution was passed through the filter 7 at a flow rate of 5 ml/min to wash away erythrocytes. Then, an injector charged with 2 ml of physiological saline solution was attached to an outlet opening 15 of the filter 7 and the physiological saline solution was violently injected into the filter 7 to cause the leukocytes entrapped in the filter 7 to flow out violently from the filter 7. When the recovered liquid was examined, it was found that 40% of leukocytes were recovered and the number of erythrocytes incorporated in the recovered leukocytes was 1/5 of the number of recovered leukocytes, which corresponded to a concentration of 600/micro-liter.

COMPARATIVE EXAMPLE 1

The experiment was carried out in the same manner as described in Example 1 except that polyvinylpyrrolidone (having a molecular weight of 40,000) having a dissolution rate of 1.2 mg/min·cm$^2$ in water was used instead of the polyvinylpyrrolidone (having a molecular weight of 360,000) having a dissolution rate of 0.62 mg/min·cm$^2$, which was used in Example 1. Leukocytes were recovered at a recovery ratio of 42%, but the number of incorporated erythrocytes was 5.8 times the number of recovered leukocytes, which corresponded to a concentration of 18,000/micro-liter.

COMPARATIVE EXAMPLE 2

The experiment was carried out in the same manner as described in Example 1 except that the physiological saline solution of polyvinylpyrrolidone was not filled at all. Luekocytes were recovered at a recovery ratio of 44%, but the number of incorporated erythrocytes was 7.6 times the number of recovered leukocytes, which corresponded to a concentration of 25,000/micro-liter.

EXAMPLE 2

The experiment was carried out in the same manner as described in Example 1 except that an aqeous physiological saline solution containing 3.5 g/dl of sodium casein having a dissolution rate of 0.63 mg/min·cm$^2$ in water was used instead of the aqueous physiological saline solution containing 2.5 g/dl of polyvinypyrrolidone having a dissolution rate of 9.62 mg/min·cm$^2$ in water. Leukocytes were recovered at a recovery ratio of 39%, and the number of incorporated erythrocytes was 1/6 of the number of recovered leukocytes, which corresponded to a concentration of 500/micro-liter.

EXAMPLE 3

The experiment was carried out in the same manner as described in Example 1 except that an aqueous physiological saline solution containing 3.5 g/dl of polyvinylalcohol (having a polymerization degree of 500) having a dissolution rate of 0.61 mg/min·cm$^2$ in water was used instead of the aqueous physiological saline solution containing 2.5 g/dl of polyvinylpyrrolidone having a dissolution rate of 0.62 mg/min·cm$^2$ in water. Leukocytes were recovered at a recovery ratio of 42%, and the number of incorporated erythrocytes was ⅛ of the number of recovered leukocytes, which corresponded to a concentration of 400/micro-liter.

COMPARATIVE EXAMPLE 3

The experiment was carried out in the same manner as that described in Example 3 except that polyvinylalcohol (having a degree of polymerization of 1,200) having a dissolution rate of 0.27 mg/min·cm$^2$ in water was used instead of the polyvinylalcohol (having a degree of polymerization of 500) having a dissolution rate of 0.61 mg/min·cm$^2$. Leukocytes were recovered at a recovery ratio of 40%, but the number of incorporated erythrocytes was substantially equal to the number of recovered leukocytes, which corresponded to a concentration of 3,000/micro-liter.

EXAMPLE 4

The experiment was carried out in the same manner as described in Example 1 except that an aqueous physiological saline solution containing 3.5 g/dl of gelatin (having a molecular weight of 60,000) having a dissolution rate of 0.62 mg/min·cm$^2$ in water was used instead of the aqueous physiological saline solution, containing 2.5 g/dl of polyvinylpyrrolidone having a dissolution rate of 0.62 mg/min·cm$^2$ in water. Leukocytes were recovered at a recovery ratio of 38%, and the number of incorporated erythrocytes was 1/29 of the number of recovered leukocytes, which corresponded to a concentration of 100/micro-liter.

COMPARATIVE EXAMPLE 4

The experiment was carried out in the same manner as described in Example 4 except that instead of the gelatin (having a molecular weight of 60,000) having a dissolution rate of 0.62 mg/min·cm$^2$ in water, there was used a decomposition product (having a molecular weight of 4,000 to 7,000) obtained by enzymatically decomposing the above gelatin, which had a dissolution rate of 1.15 mg/min·cm$^2$ in water. Leukocytes were recovered at a recovery ratio of 40%, but the number of incorporated erythrocytes was 8 times the number of recovered leukocytes, which corresponded to a concentration of 24,000/micro-liter.

EXAMPLE 5

The experiment was carried out in the same manner as described in Example 4 except that instead of the gelatin (having a molecular weight of 60,000) having a dissolution rate of 0.62 mg/min·cm$^2$ in water, there was used a decomposition product (having a molecular weight of 30,000) obtained by decomposing the above gelatin under heating, which had a dissolution rate of 0.93 mg/min·cm$^2$ in water. Leukocytes were recovered at a recovery ratio of 40%, and the number of incorporated erythrocytes was 1/7 of the number of recovered leukocytes, which corresponded to a concentration of 900/micro-liter.

COMPARATIVE EXAMPLE 5

The experiment was carried out in the same manner as that described in Example 4 except that after the fibers had been coated with the gelatin (having a molecular weight of 60,000) having a dissolution rate of 0.62 g/min·cm$^2$ in water, the gelatin on the surfaces of the fibers was cross-linked and insolubilized to water by an aqueous 2% solution of glutaraldehyde and then, the coated fibers were used as the separating material. Leukocytes were recovered at a recovery ratio of 44%, by the number of incorporated erythrocytes was 5.4 times the number of recovered leukocytes, which corresponded to a concentration of 18,000/micro-liter.

EXAMPLE 6

The experiment was carried out in the same manner as described in Example 1 except that an aqueous physiological saline solution containing 3.5 g/dl of polymetyhl vinyl ether having a dissolution rate of 0.57 mg/min·cm$^2$ in water was used instead of the aqueous physiological saline solution containing 2.5 g/dl of polyvinylpyrrolidone having a dissolution rate of 0.62 mg/min·cm$^2$ in water. Leukocytes were recovered at a recovery ratio of 40%, and the number of incorporated erythrocytes was 1/5 of the number of recovered leukocytes, which corresponded to a concentration of 700/micro-liter.

EXAMPLE 7

The experiment of collecting lymphocytes was carried out by using the apparatus illustrated in FIG. 8. A leukocyte-separating filter 7 was prepared by packing 0.3 g of a leukocyte-separating material in a container having an inner diameter of 10 mm and a length of 26 mm. The preparation of the leukocyte-separating filter was conducted according to the following procedures.

Figure 10:
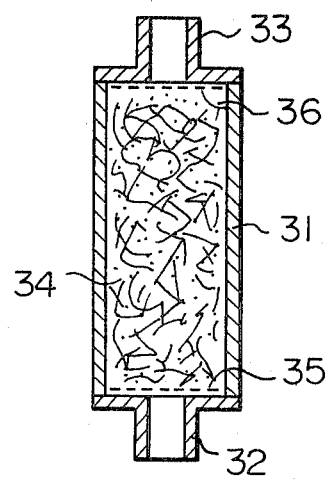
FIG. 10 is a schematic sectional view illustrating an embodiment of the leukocyte-separating filter according to the present invention prior to formation of a coating layer.

As illustrated in FIG. 10, a cylindrical pipe 31 having an inner cavity having an inner diameter of 10 mm and a length of 25 mm and caps 32 and 33 provided with a nozzle, which are engaged with openings formed on both ends of the cylindrical pipe 31, were prepared and used.

As well as the fibrous material 34, there were used 0.26 g of polyacrylonitrile fibers having an average diameter of 8 microns. The fibers were sufficiently opened before they were actually used.

The cap 32 was bonded to the cylindrical pipe 31, and a mesh net 35 was disposed so as to prevent protrusion of the fibers from the cylindrical pipe 31. The open fibers were uniformly packed into the cylindrical pipe 31 and another mesh net 36 was placed. The cap 33 was placed on the pipe 31 and bonded thereto.

Figure 11:
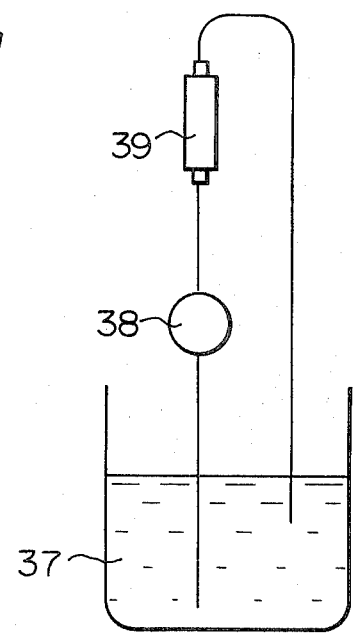
FIG. 11 is a diagram illustrating an embodiment of the apparatus that is used for formation of a coating layer.

Then, as shown in FIG. 11, the so formed filter 39 was attached to an apparatus for circulating a coating substance 37 by means of a pump 38.

A 7% by weight solution of gelatin (having a molecular weight of 110,000) having a dissolution rate of 0.49 mg/min·cm$^2$ was used as the coating substance 37, and the solution was circulated through the interior of the filter 39 at a flow rate of 5 ml/min at room temperature for about 2 minutes by means of the pump 38. During this circulation, the filter 39 was lightly tapped to remove air from the filter sufficiently.

Figure 12:
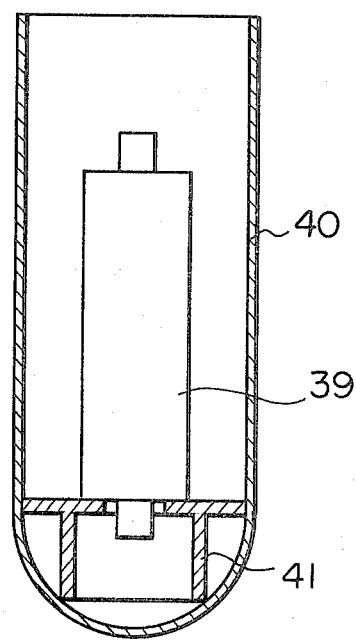
FIG. 12 is a diagram illustrating an embodiment of the means that is used for removing a surplus amount of the coated substance.

Then as shown in FIG. 12, a spacer 51 was inserted into a centrifuge tube 40, and the filter 39 was vertically erected. Centrifugal separation was carried out at room temperature for 5 minutes under a centrifugal force of 350×g by using a swing rotor type centrifugal separator to remove the surplus amount of the gelatin solution. Then, the filter was placed in a vacuum drier and dried at room temperature for 24 hours. After centrifugal separation, the fibers in pipe 31 were not shrunk, and after drying, a coating layer of gelatin was formed entirely on the surface of the fibrous material (the embedded cut piece of the coated fibers was prepared and observed by a transmission type electron microscope).

A filter 16 for separating monocytes and granulocytes shown in FIG. 8, was prepared by packing 0.88 g of a fleece-like mass of polyamide fibers having an average diameter of 20.8 microns into a vessel having an inner diameter of 10 mm and a length of 75 mm.

Referring to FIG. 8, physiological saline solution 10 was introduced into the filter 16 for entrapping monocytes and granulocytes and the leukocyte-separating filter 7 by means of the pump 8, and then, the inlet conduit 11 was transferred to the vessel 12 and 5 ml of heparin-added human blood 13 maintained at 37° C. was fed to the filter 16 for entrapping monocytes and granulocytes at a flow rate of 1 ml/min. Then, the inlet conduit 11 was transferred to the vessel 17, and a silicone oil 18 was passed at a flow rate of 1 ml/min to transfer the blood left in the filter 16 toward the leukocyte-separating filter 7. Then, the filter 16 for entrapping monocytes and granulocytes was taken out and 20 ml of physiological saline solution 10 was fed at a flow rate of 5 ml/min to the leukocyte-separating filter 7 from the inlet conduit 19 thereof to wash the filter 7. Then, the leukocyte-separating filter 7 was taken out and an injector charged with 2 ml of physiological saline solution was attached to the inlet conduit 19 of the leukocyte-separating filter 7. The physiological saline solution in the injector was violently injected into the filter 7 and the leukocytes entrapped in the filter 7 were caused to quickly flow out from the filter 7. When the recovered liquid was inspected, it was found that lymphocytes were recovered at a recovery ratio of 15%, and the ratio of incorporation of monocytes and granulocytes was 8% based on the lympocytes. Each of the numbers of incorporated erythrocytes and platelets was 1/10 of the number of recovered lymphocytes. The erythrocyte concentration was 75/micro-liter.

COMPARATIVE EXAMPLE 6

The experiment was carried out in the same manner as described in Example 1 except that the polyacrylonitrile fibers were not coated with the aqueous solution of gelatin. Lymphocytes were recovered at a recovery ratio of 14%, and the ratio of incorporation of monocytes and granulocytes into lympocytes was 6%, but the number of incorporated erythrocytes was 14 times the number of recovered lymphocytes and the number of incorporated platelets was 4/10 of the number of recovered lymphocytes. The erythrocyte concentration was 10,000/micro-liter.

COMPARATIVE EXAMPLE 7

A leukocyte-separating filter was prepared by passing a bundle of polyacrylonitrile filaments each having an average diameter of 8 microns in the flatly spread state through a tank filled with an aqueous 7% by weight solution of the same gelatin as used in Example 7, and the coated surfaces of the fibers were dried with hot air and the fibers were wound. Then, the fibers were sufficiently dried and crimped, and were opened by using a carding machine. The opening operation was performed conveniently, but the gelatin coating was separated here and there from the surfaces of the fibers (separation was observed by observation under scanning type and transmission type electron microscopes).

COMPARATIVE EXAMPLE 8

Polyacrylonitrile fibers having an average diameter of 8 microns were opened and dipped in an aqueous 7% by weight solution of the same gelatin as used in Example 7. The fibers were taken out from the solution, centrifuged and opened. However, since drying was not conducted before opening, the opening operation could not be performed conveniently because the fibers were bonded to one another. Therefore, the fibers were dried at 50° C. for 16 hours and then they were opened again. When the fibers were examined by scanning type and transmission type electron microscopes, it was found that the gelatin coating had been separated here and there from the surfaces of the fibers.

EXAMPLE 8

In the same experimental apparatus as used in Example 1, the experiment was carried out in the same manner as described in Example 7 except that casein was used instead of gelatin. The dissolution rate of the casein used in the experiment was 0.43 mg/min·cm$^2$ in water. Lymphocytes were recovered at a recovery ratio of 18%, and the number of incorporated erythrocytes was 1/5 of the number of recovered lymphocytes, which corresponded to an erythrocyte concentration of 180/micro-liter.

EXAMPLE 9

Using the same experimental apparatus as used in Example 7, the experiment was carried out in the same manner as described in Example 7 except that an aqueous solution containing 3.5 g/liter or polyvinylalcohol was used instead of the aqueous solution containing 7 g/dl of gelatin. The dissolution rate of the polyvinylalcohol used in the experiment was 0.77 mg/min·cm$^2$ in water. Lymphocytes were recovered at a recovery ratio of 16%. The number of incorporated erythrocytes was $\frac{1}{4}$ of the number of recovered lymphocytes, which corresponded to an erythrocyte concentration of 200/micro-liter.

EXAMPLE 10

Using the same experimental apparatus as used in Example 7, 3.3 g of a fleece-like mass of polyester fibers having an average diameter of 8.5 microns were packed into a container having an inner diameter of 18 mm and a length of 100 m, and an aqueous physiological saline solution containing 2 g/dl of polyvinylpyrrolidone was packed in the vessel to form a leukocyte-separating filter. The dissolution rate of this polyvinylpyrrolidone was 0.5 mg/min·cm$^2$ in water. Then 100 ml of heparin-added human blood was passed through the so formed leukocyte-separating filter at a flow rate of 5 ml/min, and 200 ml of physiological saline solution was then passed through the filter at a flow rate of 10 ml/min to wash away eryhthrocytes. Then, 100 ml of a plasma-containing physiological solution was passed through the filter at a flow rate of 10 ml/min and leukocytes in the filter were recovered while imparting a physical external force to the filter. When the recovered liquid was inspected, it was found that leukocytes were recovered at a recovery ratio of 54% and the number of incorporated erythrocytes was 1/13 of the number of recovered leukocytes, which corresponded to an erythrocyte concentration of 200/micro-liter.

EXAMPLE 11

The experiment was carried out under the same conditions as adopted in Example 10 except that 6 g of polyester fibers having an average diameter of 13.5 microns were used as the fibrous substrate. Leukocytes were recovered at a recovery ratio of 40%, and the number of incorporated erythrocytes was 2/5 of the number of recovered leukocytes, which corresponded to an erythrocyte concentration of 800/micro-liter.

As will be apparent from the foregoing illustration, when leukocytes were collected from a leukocyte-containing suspension according to the leukocyte-separating process of the present invention, the number of erythrocytes incorporated in recovered leukocytes can be reduced drastically, and also the number of incorporated platelets can be reduced. Furthermore, the separation can be accomplished by simple operations and the time required for completion of the separation can be shortened. Therefore, leukocytes are not influenced by the separation treatment. It has been confirmed that if leukocytes recovered according to this invention are used for various clinical tests and examinations, the reliability can be sufficiently enhanced.

We claim:

1. A material for separating leukocytes from a leukocyte-containing suspension, which comrises a fibrous material having a surface layer coated on the fibrous material, said surface layer consisting essentially of a substance which is capable of being dissolved by degrees in water at a dissolution rate in water of from 0.3 to 1.0 mg/min·cm$^2$ at a temperature of 30° C.

2. The leukocyte-separating material according to claim 1, wherein the substance of the surface layer is in a dried state.

3. The leukocyte-separating material according to claim 1, wherein the dissolution rate in water is from 0.4 to 0.9 mg/min·cm$^2$.

4. The leukocyte-separating material according to claim 1, wherein the substance coated on the fibrous material is at least one substance selected from the group consisting of polyvinyl alcohol, polyvinyl pyrrolidone, poly-methyl vinyl ether, casein and gelatin.

5. The leukocyte-separating material according to claim 1, wherein the fibrous material is at least one material selected from the group consisting of synthetic fibers, semi-synthetic fibers, regenerated cellulose fibers, natural fibers and inorganic fibers.

6. The leukocyte-separating material according to claim 1, wherein the fibrous material has an average fiber diameter of not more than 60 microns.

7. The leukocyte-separating material according to claim 6, wherein the average fiber diameter is in the range of from 5 microns to 10 microns.

8. A filter for separating leukocytes from a leukocyte-containing suspension, which comprises the leukocyte-separating material, as claimed in claim 1, packed in a container.

9. The leukocyte-separating filter according to claim 8, which comprises a fibrous material having an average fiber diameter of from 5 to 10 microns and packed in a container at a bulk density of from 0.04 to 0.25 g/cm$^3$, said fibrous material having a surface layer composed of a substance exhibiting a dissolution rate in water of from 0.4 to 0.9 mg/min·cm$^2$.

10. The leukocyte-separating filter according to claim 9, wherein said fibrous material is composed of synthetic fibers and packed in a dried state in the container, and, the coating substance is polyvinyl alcohol and/or gelatin.

11. The leukocyte-separating filter according to claim 8, wherein the leukocyte-separating material is packed in the container at a bulk density of from 0.04 to 0.4 g/cm$^3$.

12. A material for separating leukocytes from a leukocyte-containing suspension, which comprises synthetic fibers having an average fiber diameter of from 5 microns to 10 microns, said synthetic fibers having a polyvinylalcohol and/or gelatin surface layer which exhibits a dissolution rate in water of from 0.4 to 0.9 mg/min·cm$^2$ at a temperature of 30° C. and is in a dried state.

13. A filter for separating lymphocytes from a lymphocyte-containing suspension, which comprises at least one container packed with fibers and having at least two inlet and outlet openings, said container or containers have a first portion composed of fibers having an average diameter of from 5 to 20 microns, which fibers are packed at a bulk density of from 0.04 g/cm$^3$ and which fibers have a surface layer coated thereon and consisting essentially of a substance capable of being dissolved in water by degrees and exhibits a dissolution rate in water of from 0.3 to 1.0 mg/min·cm$^2$ at a temperature of 30° C., and a second portion arranged in series to said first portion and composed of fibers having an average diameter larger than the average diameter of the fibers of the first portion and in the range of from 10 to 60 microns.

14. The lymphocyte-separating filter according to claim 13, wherein the dissolution rate in water is in the range of from 0.4 to 0.9 mg/min·cm$^2$.

15. The lymphocyte-separating filter according to claim 13, wherein the water-soluble substance on the fibers is at least one substance selected from the group consisting of polyvinyl alcohol, polyvinyl pyrrolidone, poly-methyl vinyl ether, casein and gelatin.

16. The lymphocyte-separating filter according to claim 13, wherein the fibers are comprised of at least one type of fibers selected from the group consisting of synthetic fibers, semi-synthetic fibers, regenerated cellulose fibers, natural fibers and inorganic fibers.

17. The lymphocyte-separating filter according to claim 13, wherein the fibers in said first portion have an average fiber diameter of from 5 to 10 microns and are packed at a bulk density of from 0.04 to 0.25 g/cm$^3$.

18. The lymphocyte-separating filter according to claim 13, wherein the water-soluble substance on the fibers in the first portion is in a dried state.

19. The lymphocyte-separating filter according to claim 18, wherein the fibers in said first portion have a polyvinyl alcohol and/or gelatin surface layer exhibiting a dissolution rate in a water of from 0.4 to 0.9 mg/min·cm$^2$, have an average fiber diameter of from 5 to 10 microns, and are packed at a bulk density of from 0.04 to 0.25 g/cm$^3$.

* * * * *